US00PP24493P3

(12) United States Plant Patent
Head et al.

(10) Patent No.: US PP24,493 P3
(45) Date of Patent: May 27, 2014

(54) AZALEA PLANT NAMED 'RLH1-10P18'

(50) Latin Name: *Rhododendron hybrida*
Varietal Denomination: RLH1-10P18

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select, Inc., Seneca, SC (US)

( * ) Notice: Subject to any disclaimer, the term of this patent is extended or adjusted under 35 U.S.C. 154(b) by 0 days.

(21) Appl. No.: 13/573,833

(22) Filed: Oct. 8, 2012

(65) Prior Publication Data

US 2014/0101805 P1 Apr. 10, 2014

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Kent L Bell
(74) *Attorney, Agent, or Firm* — C. A. Whealy

(57) ABSTRACT

A new and distinct cultivar of Azalea plant named 'RLH1-10P18', characterized by its upright to outwardly spreading and mounding plant habit; freely basal branching habit; dense and bushy appearance; vigorous growth habit and rapid growth rate; evergreen, persistent dark green-colored leaves that do not abscise during the winter; freely flowering habit with remontant flowering during the spring, summer and autumn; large, non-persistent semi-double to double flowers that are dark red in color with darker red-colored central spots and speckles; and excellent garden performance and temperature tolerance.

1 Drawing Sheet

Botanical designation: *Rhododendron hybrida.*
Cultivar denomination: 'RLH1-10P18'.

BACKGROUND OF THE INVENTION

The present Invention relates to a new and distinct cultivar of Azalea plant, botanically known as *Rhododendron hybrida*, commercially referred to as an evergreen Azalea plant and hereinafter referred to by the name 'RLH1-10P18'.

The new Azalea plant is a product of a planned breeding program conducted by the Inventors in Long Creek, Oconee County, S.C. The objective of the breeding program is to create new compact evergreen Azalea plants having dense growth habit, large attractive flowers, flowers with good temperature tolerance, consistent remontant flowering during the spring, summer and autumn, good garden performance and low and high temperature tolerance.

The new Azalea plant originated from a cross-pollination made by the Inventors in 1996 in Long Creek, Oconee County, S.C., of a proprietary selection of *Rhododendron hybrida* identified as code number RLH-1900-RP, not patented, as the female, or seed, parent with a proprietary selection of *Rhododendron hybrida* identified as code number HO-18-SGY, not patented, as the male, or pollen, parent. The new Azalea plant was discovered and selected by the Inventors as a single flowering plant within the progeny of the stated cross-pollination in a controlled greenhouse environment in Long Creek, Oconee County, S.C. in 2000.

Asexual reproduction of the new Azalea plant by semi-hardwood stem cuttings taken in a controlled greenhouse environment in Long Creek, Oconee County, S.C. since 2005 has shown that the unique features of this new Azalea plant are stable and reproduced true to type in successive generations.

SUMMARY OF THE INVENTION

Plants of the new Azalea have not been observed under all possible environmental conditions and cultural practices. The phenotype may vary somewhat with variations in environmental conditions such as temperature, daylength and light intensity without, however, any variance in genotype. The following traits have been repeatedly observed and are determined to be the unique characteristics of 'RLH1-10P18'. These characteristics in combination distinguish 'RLH1-10P18' as a new and distinct Azalea plant:

1. Upright to outwardly spreading and mounding plant habit.
2. Freely basal branching habit; dense and bushy appearance; vigorous growth habit and rapid growth rate.
3. Evergreen, persistent dark green-colored leaves that do not abscise during the winter.
4. Freely flowering habit with remontant flowering during the spring, summer and autumn.
5. Large, non-persistent semi-double to double flowers that are dark red in color with darker red-colored central spots and speckles.
6. Excellent garden performance and temperature tolerance.

Plants of the new Azalea differ primarily from plants of the female parent selection in the following characteristics:

1. Plants of the new Azalea are more spreading than and not as globose as plants of the female parent selection.
2. Plants of the new Azalea are more freely branching than plants of the female parent selection.
3. Plants of the new Azalea have much larger flowers than plants of the female parent selection.
4. Plants of the new Azalea have semi-double to double flowers whereas plants of the female parent selection have single to semi-double flowers.

5. Plants of the new Azalea flower during the spring, summer and autumn whereas plants of the female parent selection only flower during the spring and autumn.
6. Plants of the new Azalea and the female parent selection differ in flower color as plants of the female parent selection have red purple-colored flowers.

Plants of the new Azalea differ primarily from plants of the male parent selection in the following characteristics:

1. Plants of the new Azalea have semi-double to double flowers whereas plants of the male parent selection have single flowers.
2. Plants of the new Azalea flower during the spring, summer and autumn whereas plants of the male parent selection flower during the spring and only sporadically during the summer and autumn.
3. Plants of the new Azalea and the male parent selection differ in flower color as plants of the male parent selection have red purple-colored flowers.

Plants of the new Azalea can be compared to the plants of 'Robleg', disclosed in U.S. Plant Pat. No. 15,227. In side-by-side comparisons conducted in Long Creek, Oconee County, S.C., plants of the new Azalea differed primarily from plants of 'Robleg' in the following characteristics:

1. Plants of the new Azalea were more uniform in plant shape and required less pruning to maintain a more uniform plant shape than plants of 'Robleg'.
2. Plants of the new Azalea were more freely flowering than plants of 'Robleg'.
3. Plants of the new Azalea had semi-double to double flowers whereas plants of 'Robleg' had single flowers.
4. Plants of the new Azalea and 'Robleg' differed in flower color as plants of 'Robleg' had white-colored flowers.
5. Plants of the new Azalea flowered during the spring, summer and autumn whereas plants of 'Robleg' only flowered during the spring and autumn.
6. Plants of the new Azalea were more cold hardy than plants of 'Robleg'.

BRIEF DESCRIPTION OF THE PHOTOGRAPH

The accompanying colored photograph illustrates the overall appearance of the new Azalea plant showing the colors as true as it is reasonably possible to obtain in colored reproductions of this type. Colors in the photograph may differ slightly from the color values cited in the detailed botanical description which accurately describe the colors of the new Azalea plant. Plants used for the photograph were grown during the late summer in ground beds in a shady outdoor nursery in Long Creek, Oconee County, S.C. and under cultural practices which approximate commercial Azalea production. During the production of the plants, day temperatures ranged from 0° C. to 45° C. and night temperatures ranged from −17° C. to 38° C. Plants were seven years old when the photograph were taken.

The photograph comprises a top perspective view of a typical flowering plant of 'RLH1-10P18'.

DETAILED BOTANICAL DESCRIPTION

The following observations and measurements describe plants grown during the late summer in three-gallon containers in a shadehouse in El Campo, Tex. and under cultural practices which approximate commercial Azalea production. During the production of the plants, day temperatures averaged 24° C. and night temperatures averaged 14° C. Plants were one year old when the detailed description was taken. In the following description, color references are made to The Royal Horticultural Society Colour Chart, 2007 Edition, except where general terms of ordinary dictionary significance are used.

Botanical classification: *Rhododendron hybrida* 'RLH1-10P18'.

Commercial classification: Evergreen Azalea.

Parentage:

*Female, or seed, parent*.—Proprietary selection of *Rhododendron hybrida* identified as code number RLH-1900-RP, not patented.

*Male, or pollen, parent*.—Proprietary selection of *Rhododendron hybrida* identified as code number HO-18-SGY, not patented.

Propagation:

*Type*.—By semi-hardwood stem cuttings.

*Time to initiate roots, summer*.—About 25 to 30 days at temperatures of 27° C. to 30° C.

*Time to initiate roots, winter*.—About 35 to 45 days at temperatures of 16° C. to 17° C.

*Time to produce a rooted young plant, summer*.—About 60 to 70 days at temperatures of 27° C. to 30° C.

*Time to produce a rooted young plant, winter*.—About 80 to 100 days at temperatures of 16° C. to 17° C.

*Root description*.—Fine, fibrous; initially white in color becoming light brown with development.

*Rooting habit*.—Freely branching; dense.

Plant description:

*Plant form, plant and growth habit*.—Perennial and evergreen flowering subshrub; upright to outwardly spreading and mounding plant habit; vigorous growth habit; rapid growth rate; freely flowering habit with numerous semi-double to double flowers.

*Branching habit*.—Freely branching habit with lateral branches potentially developing at every node; dense and bushy appearance; pinching (removal of terminal apex) enhances lateral branch development.

*Plant height, soil level to top of flowers*.—About 25 cm.

*Plant diameter, area of spread*.—About 52 cm.

*Lateral branch description*.—Length: About 15 cm. Diameter at base: About 5 mm. Internode length: About 7.5 mm. Strength: Strong. Aspect: Upright and outwardly positioned. Texture, developing: Pubescent, fine greyed orange-colored hairs. Texture, mature: Woody; pubescent, fine greyed orange-colored hairs. Color, developing: Close to 165A to 165B. Color, semi-hardwood: Close to 165A to 165B. Color, mature: Close to 165A.

*Leaf description*.—Arrangement: Alternate; simple. Leaf retention: Very good winter leaf retention has been observed on plants of the new Azalea. Length: About 4.9 cm. Width: About 2.2 cm. Shape: Oblanceolate to elliptic. Apex: Acute; mucronate. Base: Cuneate to attenuate. Margin: Entire; ciliate. Venation pattern: Pinnate; reticulate. Texture, upper and lower surfaces: Pubescent; coriaceous, tough. Color: Developing and fully expanded leaves, upper surface: Close to 147A; venation, close to 144A. Developing and fully expanded leaves, lower surface: Close to 147B; venation, close to 146B to 146C. Petioles: Length: About 8 mm. Diameter: About 2 mm. Texture, upper and lower surfaces: Pubescent. Color, upper surface: Close to 144A. Color, lower surface: Close to 146B to 146C.

Flower description:

*Natural flowering season*.—Spring, April to May, and then remontant flowering during the summer and autumn, July to October or until frost in USDA Hardiness Zone 6.

*Flower appearance and arrangement*.—Semi-double to double rose-shaped flowers arranged upwardly to outwardly in clusters at terminals and sub-terminals; outer whorl of five petals and inner whorl with two to five staminate petaloids.

*Flowering habit*.—Freely flowering habit with usually about four to five flowers per cluster.

*Flower longevity*.—Flowers are durable and long-lasting; depending on the temperature, flowers last about one week on the plant; flowers not persistent.

*Fragrance*.—None detected.

*Flower diameter*.—About 8 cm.

*Flower depth*.—About 3.75 cm.

*Flower buds* (*before showing color*).—Length: About 1.6 cm. Diameter: About 7.5 mm. Shape: Ovoid. Color: Close to 144A to 144B.

*Petals, outer whorl*.—Length: About 5.1 cm. Width: About 3.5 cm. Shape: Broadly ovate to orbicular. Apex: Rotund; undulate. Margin: Entire; undulate, ruffled appearance. Texture, upper and lower surfaces: Smooth, glabrous; waxy to velvety in appearance. Color: When opening and fully opened, upper surface: Between 45A and 46B; central spots and speckles, close to 53A; color becoming closer to 53C with development. When opening and fully opened, lower surface: Between 45A and 46B.

*Petaloids, inner whorl*.—Length: About 3.7 cm. Width: About 2.1 cm. Shape: Broadly ovate to orbicular; mostly irregular in shape. Apex: Rotund; undulate. Margin: Entire; undulate, ruffled appearance. Texture, upper and lower surfaces: Smooth, glabrous; rugulose; waxy to velvety in appearance. Color: When opening and fully opened, upper surface: Between 45A and 46B; central spots and speckles, close to 53A; color becoming closer to 53C with development. When opening and fully opened, lower surface: Between 45A and 46B.

*Sepals*.—Arrangement: Five in a single whorl, fused at the base forming a campanulate to star-shaped corona. Length: About 1.2 cm. Width: About 4 mm. Shape: Lanceolate. Apex: Acute. Base: Truncate. Margin: Entire; ciliate. Texture, upper and lower surfaces: Densely pubescent. Color, upper and lower surfaces: Close to 144A to 144B.

*Peduncles*.—Length: About 1.2 cm. Diameter: About 2.5 mm. Angle: Mostly upright. Strength: Strong. Texture: Pubescent. Color: Close to 144A to 144B; distally, overlain with close to 53A and 60A.

*Reproductive organs*.—Androecium: Quantity of stamens per flower: About two; typically transformed into petaloids. Filament length: About 2.4 cm. Filament color: Close to 46A. Anther shape: Porandrous with four oblong, tubular to lunate-shaped pollen sacks basifixed to the filament. Anther length: About 2 mm. Anther color: Close to N186C. Pollen amount: None. Gynoecium: Pistil length: About 5.1 cm. Stigma shape: Round to flattened (capitate). Stigma color: Close to N79B. Style length: About 4.8 cm. Style color: Close to 53A. Ovary color: Close to 187B.

*Fruits and seeds*.—Fruit and seed development have not been observed on plants of the new Azalea.

Garden performance & temperature tolerance: Plants of the new Azalea have been observed to be very tolerant to rain, wind and temperatures ranging from about −25° C. to about 45° C.; and plants of the new Azalea are suitable for USDA Hardiness Zones 6 to 9.

Disease & pest resistance: Plants have not been observed to be resistant to pathogens and pests common to Azalea plants.

It is claimed:

1. A new and distinct cultivar of Azalea plant named 'RLH1-10P18' as illustrated and described.

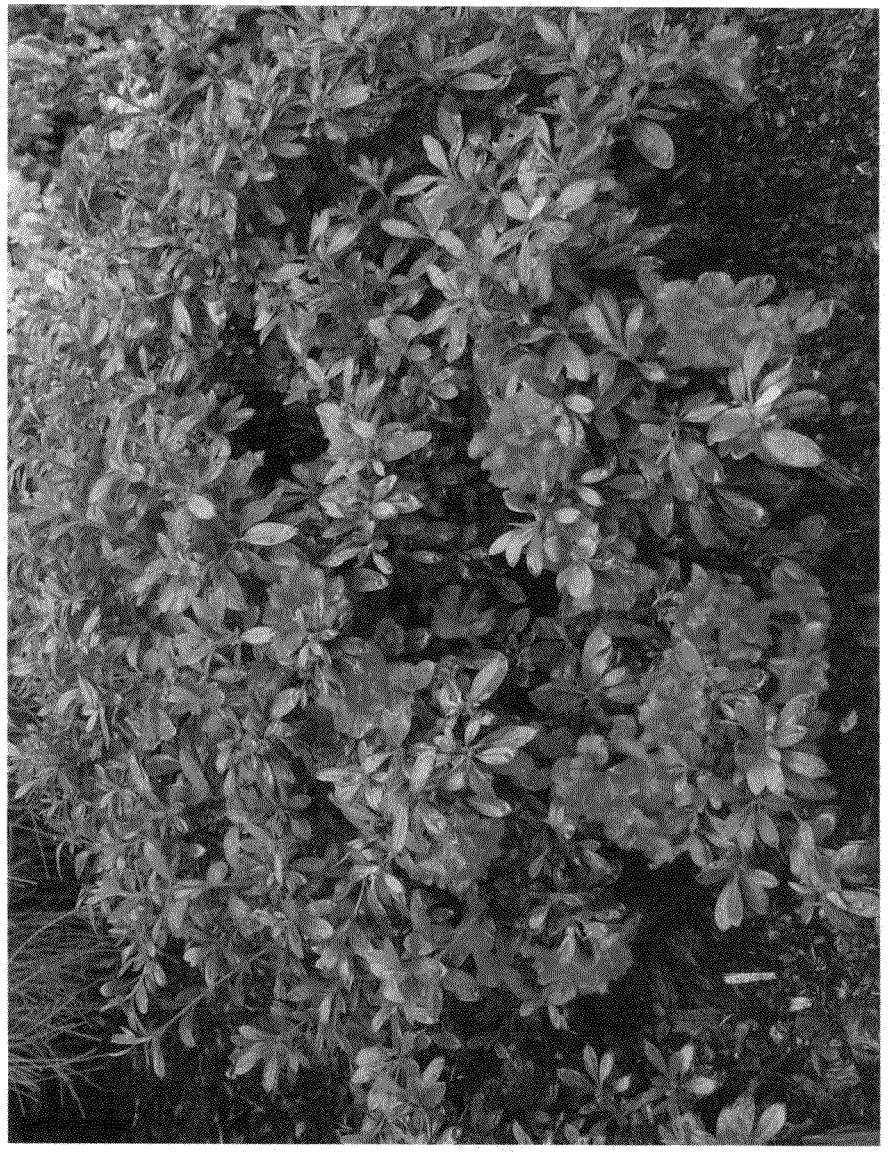

* * * * *